United States Patent [19]

Borchardt et al.

[11] Patent Number: 5,858,251
[45] Date of Patent: Jan. 12, 1999

[54] CONCENTRATION OF WATERBORNE PATHOGENIC ORGANISMS

[75] Inventors: Mark A. Borchardt, Marshfield; Susan K. Spencer, Spencer, both of Wis.

[73] Assignee: Marshfield Medical Research and Education Foundation, A Division of Marshfield Clinic, Marshfield, Wis.

[21] Appl. No.: 909,462

[22] Filed: Aug. 11, 1997

Related U.S. Application Data

[63] Continuation-in-part of Ser. No. 608,422, Feb. 28, 1996.

[51] Int. Cl.$^6$ .................................................. B01D 1/26
[52] U.S. Cl. ........................ 210/781; 210/787; 422/72; 494/43
[58] Field of Search ................................ 216/781, 787, 216/360.1, 380.1, 43 S; 422/41, 43, 70; 209/173; 494/41, 43, 70

[56] References Cited

U.S. PATENT DOCUMENTS

| | | |
|---|---|---|
| D. 314,824 | 2/1991 | Moon . |
| 3,217,982 | 11/1965 | Wilsmann et al. . |
| 4,010,894 | 3/1977 | Kellogg et al. . |
| 4,094,461 | 6/1978 | Kellogg et al. . |
| 4,174,637 | 11/1979 | Mulzet et al. . |
| 4,217,418 | 8/1980 | McAleer et al. . |
| 4,386,730 | 6/1983 | Mulzet . |
| 4,387,848 | 6/1983 | Kellogg et al. . |
| 4,419,089 | 12/1983 | Kolobow et al. . |
| 4,430,072 | 2/1984 | Kellogg et al. . |
| 4,439,178 | 3/1984 | Mulzet . |
| 4,447,221 | 5/1984 | Mulzet . |
| 4,468,219 | 8/1984 | George et al. . |
| 4,569,759 | 2/1986 | Ben Aim et al. . |
| 4,647,279 | 3/1987 | Mulzet et el. . |
| 4,674,962 | 6/1987 | Gardineer . |
| 4,708,712 | 11/1987 | Mulzet . |
| 4,795,314 | 1/1989 | Prybella et al. . |

(List continued on next page.)

FOREIGN PATENT DOCUMENTS

| | | |
|---|---|---|
| 24 08 754 A | 4/1975 | Denmark . |
| 0 420 153 A | 3/1991 | European Pat. Off. . |
| WO 90/10057 A | 7/1990 | WIPO . |

OTHER PUBLICATIONS

Griffith, Ph.D., Owen Mitch, *Techniques of Preparative, Zonal, and Continuous Flow Ultracentrifugation*, Applications Research Dept., Spinco Division, Beckman Instruments, Inc. (1986) Booklet—50 pp.

Aldom et al., *Letters in Applied Microbiology* (1995), 20: 186–187.

Goatcher et al., *American Cancer Society of Macrobiology Abstracts* (1995) Q–212.

LeChevallier et al., *Applied and Environmental Microbiology* (1995), 61(2):690–697.

Nieminski et al., *Applied and Environmental Microbiology* (1995), 61(5):1714–1719

Vessey et al., *Journal of Applied Bacteriology* (1993), 75 : 82–86

Whitmore et al., *Wat. Sci. Tech.* (1993), 27(3–4) : 69–76.

*Primary Examiner*—David A. Reifsnyder
*Attorney, Agent, or Firm*—DeWitt Ross & Stevens S.C.

[57] ABSTRACT

A method of concentrating waterborne pathogenic organisms from water potentially contaminated by dilute densities of the organisms is described. Potentially contaminated water is directed along an elongated flow path which rests generally within a plane perpendicular to an axis of rotation, and is subjected to centrifugal forces by rotating the flow path about the rotational axis. The method may be executed by use of a conventional continuous flow channel-type blood plasmapheresis centrifuge. The method has been tested for its capability for recovering pathogenic protozoan parasites such as Cryptosporidium and Giardia from contaminated water, and recovery rates of up to 100% have been observed.

51 Claims, 5 Drawing Sheets

U.S. PATENT DOCUMENTS

| | | |
|---|---|---|
| 4,810,090 | 3/1989 | Boucher et al. . |
| 4,824,339 | 4/1989 | Bainbridge et al. . |
| 4,850,995 | 7/1989 | Tie et al. . |
| 4,861,242 | 8/1989 | Finsterwald . |
| 4,894,050 | 1/1990 | Kohlstette et al. . |
| 4,900,298 | 2/1990 | Langley . |
| 4,978,446 | 12/1990 | Lobdell . |
| 4,991,743 | 2/1991 | Walker . |
| 5,100,372 | 3/1992 | Headley ................................ 494/41 |
| 5,263,831 | 11/1993 | Kappus . |
| 5,324,629 | 6/1994 | Phi-Wilson et al. . |
| 5,352,371 | 10/1994 | Felt . |
| 5,496,265 | 3/1996 | Langley et al. . |
| 5,496,301 | 3/1996 | Hlavinka et al. . |

FIG. 1
PRIOR ART
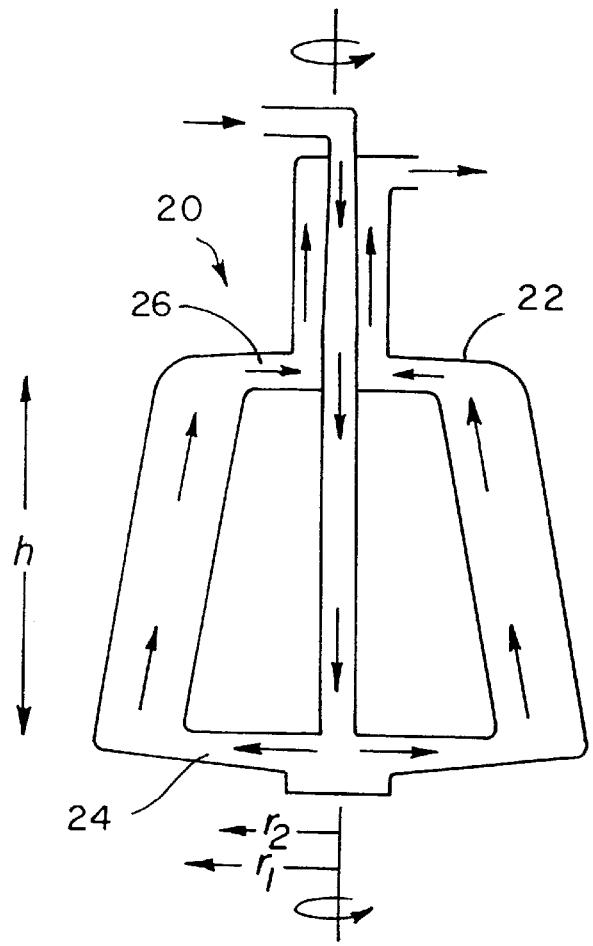
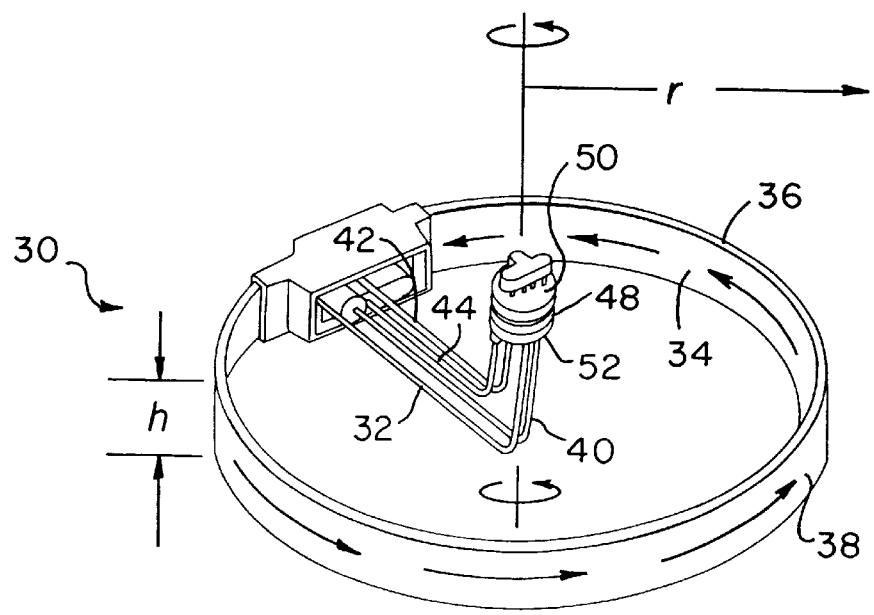
FIG. 2

CONCENTRATION OF WATERBORNE PATHOGENIC ORGANISMS

CROSS-REFERENCE TO RELATED APPLICATIONS

This application is a continuation-in-part of U.S. patent application Ser. No. 08/608,422, filed 28 Feb. 1996 now allowed, entitled Method of Concentrating Waterborne Protozoan Parasites.

FIELD OF THE INVENTION

The present invention is directed to a method of concentrating waterborne pathogenic organisms from water potentially contaminated by dilute densities of the organisms.

BACKGROUND OF THE INVENTION

Developments in water processing technology have significantly decreased the incidence of illness from waterborne pathogenic organisms. However, isolated cases of illnesses owing to such organisms are common, and occasionally large-scale outbreaks of illness occur. As an example, severe outbreaks of gastroenteritis have been caused by the environmentally resistant intestinal protozoan parasites Cryptosporidium, Giardia, Microsporidia, and Cyclospora. These organisms are often waterborne, existing in very dilute densities in public water supplies, and many have only recently been recognized as causing a health problem. As an example, Cryptosporidium has been linked to waterborne outbreaks of gastroenteritis only since 1981, when widespread cases of acute gastroenteritis in a Texas community were traced to the presence of Cryptosporidium in the drinking water supply. Numerous other cities have experienced outbreaks since then. Cryptosporidium oocysts are exemplary of waterborne protozoan parasites in that they can survive for long times in water and are resistant to routine water treatment methods such as chlorination. The presence in source waters of even small numbers of Cryptosporidium oocysts is a matter of concern because the infective dose for humans is possibly as low as one oocyst. Additionally, exposure to protozoan parasites or other waterborne pathogens can be life-threatening, particularly to infants, the elderly, and people whose immune systems are impaired. In fact, many waterborne pathogens are only now receiving significant scientific attention after having been traced to fatalities in this population, e.g., Microsporidia.

Clearly, the detection of pathogenic organisms such as Cryptosporidium in water supplies is a critical societal problem. The central issue in detection of such organisms is how to concentrate dilute densities of the organisms from large volumes of water so as to detect their presence.

Regarding protozoan parasites such as Cryptosporidium, the method currently recommended by the Environmental Protection Agency (EPA) and the American Society for Testing and Materials (ASTM) concentrates the parasites by sampling 100 liters (or more) of water through a polypropylene yarn cartridge filter. As summarized in Nieminski et al., *Applied and Environmental Microbiology*, 61(5): 1714–1719, 1995, in the ASTM method, after sampling, particulates from the cartridge filter are extracted by cutting the filter apart and washing the fibers. The extracted particulates are then concentrated by centrifugation. The concentrated particulates are then processed to selectively concentrate parasite cysts and oocysts by floatation in 50-mL tubes on a Percoll-sucrose gradient. Particulates recovered at the interface of the Percoll-sucrose gradient are stained with fluorescently tagged antibodies on 25-mm-diameter, 0.2 $\mu$m-pore-size cellulose acetate filters. After mounting on slides, the membrane filters are scanned with an epifluorescent microscope for objects having the size, shape and fluorescence characteristic of Cryptosporidium oocysts. On finding such objects, the microscope optics are switched to phase contrast to look for internal morphological characteristics inside the detected organisms. Organisms determined to meet the fluorescence detection criteria are counted as presumptive Cryptosporidium oocysts. Organisms with the right fluorescence characteristics and shown to have the respective internal morphological characteristics are counted as confirmed Cryptosporidium oocysts.

However, the ASTM method is costly and consumes substantial time and labor. It is also not very effective since losses of oocysts occur throughout the procedure. Large numbers of oocysts pass through the filter, or adhere to the filter material and are not recovered. Losses also occur during centrifugation because oocysts are destroyed or resuspended during removal of the supernatant fluid. During a recent blind test of commercial laboratories in the United States, spiked samples were submitted to sixteen laboratories to evaluate their ability to recover and detect Cryptosporidium oocysts using the ASTM method. Six laboratories—over one third of the total—failed to recover any parasites, and the remaining ten had an average recovery rate of only 2.8%. Aldom et al., *Letters in Applied Microbiology* 20: 186–187, 1995. A more detailed description of losses of Cryptosporidium oocysts during the detection procedure can be found in LeChevallier et al., *Applied and Environmental Microbiology* 61 (2): 690–697, 1995.

Several studies have been conducted on techniques to improve the efficiencies of methods for concentrating the dilute protozoa. The general protocol in such studies is to spike a water sample with a known amount of Cryptosporidium oocysts and determine the percentage of oocysts recovered for each method tested.

A number of studies evaluated other types of filtration, including vortex-flow, cross-flow, and sand column filtration. Whitmore et al., *Wat. Sci. Tech.* 27 (3–4): 69–76, 1993. In the Whitmore et al. study, the vortex-flow filtration technique gave fairly consistent recoveries of 30% to 40%. While this retention rate is superior to that of the ASTM method, the comparatively long process times would prevent the use of this method for monitoring purposes. The crossflow filtration module also gave relatively good recoveries (approximately 40–80%) at moderately high flow rates. The laboratory scale sand columns evaluated gave satisfactory retention within the column material at low flow rates, but were judged inadequate for monitoring purposes because of the poor retention of oocysts within the column matrix at realistic flow rates. Another study tested a filter matrix dissolution method to recover Cryptosporidium oocysts from water. The average recovery rate observed was 70.5%. Aldom et al., *Letters in Applied Microbiology* 20: 186–187, 1995. Cryptosporidium oocysts have also been concentrated from water by "sweeping" water with a settling calcium carbonate precipitate. Vesey et al., *Journal of Applied Bacteriology* 75: 82–86, 1993. The Vesey et al. study resulted in a 68% recovery of oocysts from seeded samples of deionized, tap, and river water.

Continuous flow bowl centrifugation has also been studied as a means to concentrate dilute concentrations of Cryptosporidium oocysts. An exemplary continuous flow bowl centrifuge commonly referred to as a Latham bowl centrifuge is shown at 20 in FIG. 1. Liquid is introduced into the end (top or bottom) of a spinning bowl 22 from an axially-directed input line 24 with length r1 located near the rotational axis of the bowl 22. As the liquid flows up the height h of the bowl 22, centrifugal force forms a density gradient in the liquid with the densest (heaviest) matter (sand or other detritus) located near the wall of the bowl 22 and the lighter matter (e.g., water) being located closer to the rotational axis. As liquid is introduced into the bowl 22, the lighter portion of the liquid is emptied at the same flow rate from an axially-situated and axially-directed exit line 26 with length r2 which exits the end of the bowl 22 opposite the input line 24. Continuous flow bowl centrifugation has been used in conjunction with heating to kill bacteria present in beverages, as described by U.S. Pat. No. 3,217,982 to Wilsmann et al. However, studies evaluating use of a continuous flow bowl centrifuge for concentrating protozoan parasites have not described increases in recovery rates. The Whitmore et al. studies cited above evaluated use of a bowl-type continuous flow centrifuge for concentration of oocysts and reported recovery between 11% to 31.2%. Goatcher et al., *American Society of Macrobiology Abstracts* Q-212, 1995 also tested a bowl-type continuous flow centrifuge system and reported obtaining recovery rates of between 2 to 20 times those observed with conventional filtration methods; therefore, such recovery rates are still well under 50%.

In view of the importance of protecting water supplies from pathogenic organisms such as protozoan parasites, and the lack of apparata or methods for concentrating and/or detecting such organisms with high recovery rates, it is clearly desirable to develop improved methods and apparata for reliably concentrating waterborne pathogenic organisms.

SUMMARY OF THE INVENTION

The present invention, which is defined by the claims set out at the end of this disclosure, is directed to the concentration of dilute densities of pathogenic organisms, e.g., protozoan parasites such as Cryptosporidium, from water. One aspect of the invention concerns a method of concentrating waterborne pathogenic organisms from water potentially contaminated by dilute densities of the organisms wherein the water is fed into an elongated flow path, e.g., a flow path defined by a channel or duct. The flow path includes a separation section wherein the water flow is oriented in directions substantially tangential with respect to a rotational axis. The flow path is then subjected to centrifugal forces by spinning it about the rotational axis in such a manner that the centrifugal forces are oriented substantially perpendicular to the separation section. This highly concentrates pathogenic organisms within the water flowing within the separation section. As will be illustrated below by experimental results, in some cases 100% recovery of Cryptosporidium oocysts has been measured.

Examples of apparata for performing this method are channel centrifuges, e.g., the IBM (COBE) model 2997 channel-type blood centrifuge (formerly made by International Business Machines, Armonk, N.Y., USA and now made by COBE, Lakewood, Colo., USA) or the COBE Spectra channel-type blood centrifuge. Such channel centrifuges, which are discussed at greater length later in this disclosure, utilize hollow hoop-shaped separation channels with the rotational axis being situated at the center of the hoop. Radially-directed input and exit lines are connected to the separation channel in much the same manner as spokes leading to a wheel. Liquid supplied to the centrifuge travels radially outward in the input line, enters the separation channel and traverses its circumference, and then travels radially inward through the exit line. When the separation channel is spun about the rotational axis, centrifugal forces oriented perpendicular to the channel are generated.

Another aspect of the invention concerns a method of concentrating waterborne pathogenic organisms from water by feeding the water into an elongated flow path which includes a separation section wherein the water flow follows an arcuate path defined about a rotational axis. Pathogenic organisms within the water in the separation section are then concentrated by spinning the flow path about the rotational axis, thereby creating centrifugal forces substantially perpendicular to the separation section. Again, exceptional recovery rates of up to 100% have been achieved. This aspect of the invention may be practiced by utilizing the channel centrifuges noted above, wherein the hoop-like channel serves as the separation section. Alternatively, it may be practiced by use of channels in the shape of ellipses, helixes, parabolic sections, or channels of other shapes which orbit or curve about the rotational axis.

A further aspect of the invention involves a method of concentrating pathogenic organisms from water by feeding the water into a flow path which includes a separation section resting within a plane (or planes) oriented generally perpendicular to the rotational axis. The separation section has a length greater than 2r, where r is the average of the maximum and minimum radial distances of the flow path from the rotational axis. Pathogenic organisms within the water in the separation section are then concentrated with up to 100% recovery rates by spinning the flow path (including the separation section) about the rotational axis, thereby subjecting it to centrifugal force. The aforementioned hoop-like channel centrifuge provides an example of a preexisting device which may be used to practice this embodiment of the method.

The various aspects of the invention summarized above have less process and apparatus/material costs, consume less time and labor, and are vastly more effective than any previously known methods and apparata for detecting pathogenic organisms such as Cryptosporidium in water. Accurate counts of contamination levels are now possible, thereby allowing effective monitoring and treatment plans to be installed. Treated water can be continuously sampled as it is being produced, thereby providing an up-to-date measure of water quality as compared to the delayed warning produced by the current method of spot-checking water supplies. Since the invention allows water treatment plants to regard organism counts with a high level of confidence, they will no longer be forced to undergo expensive repeated testing and/or remediation measures as a precautionary measure when questionably low counts are measured. Additionally, in view of the fact that the current test standard is highly unreliable (as noted by Aldom et al., supra), the invention can prevent the hardship endured by communities when outbreaks occur. Other advantages and features of the invention will be apparent from the remainder of this disclosure.

BRIEF DESCRIPTION OF THE DRAWINGS

FIG. 1 is a schematic cross-sectional view of a prior art continuous flow bowl centrifuge.

FIG. 2 is a perspective view of the channel assembly of a continuous flow channel centrifuge.

DETAILED DESCRIPTION OF THE INVENTION

Continuous Flow Channel-Type Centrifuges

Figure 3:
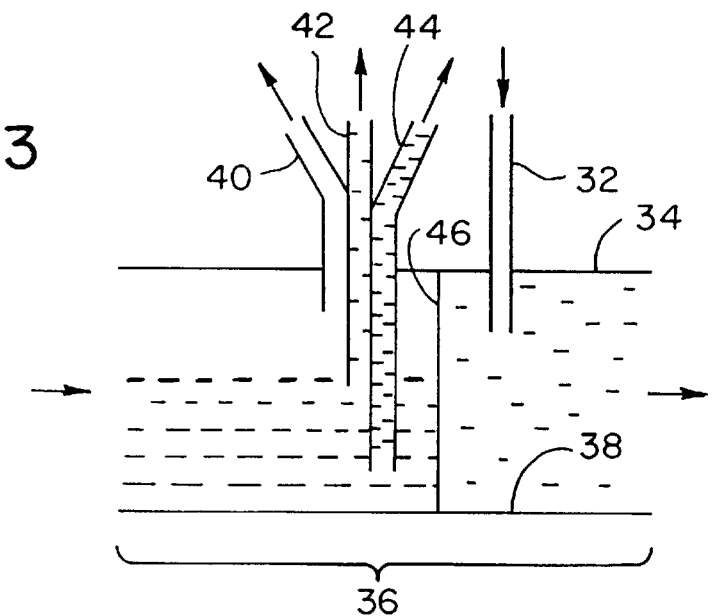
FIG. 3 is a schematic diagram of a section of the channel of FIG. 2 illustrating the channel input and outlet lines in greater detail.
Figure 4:
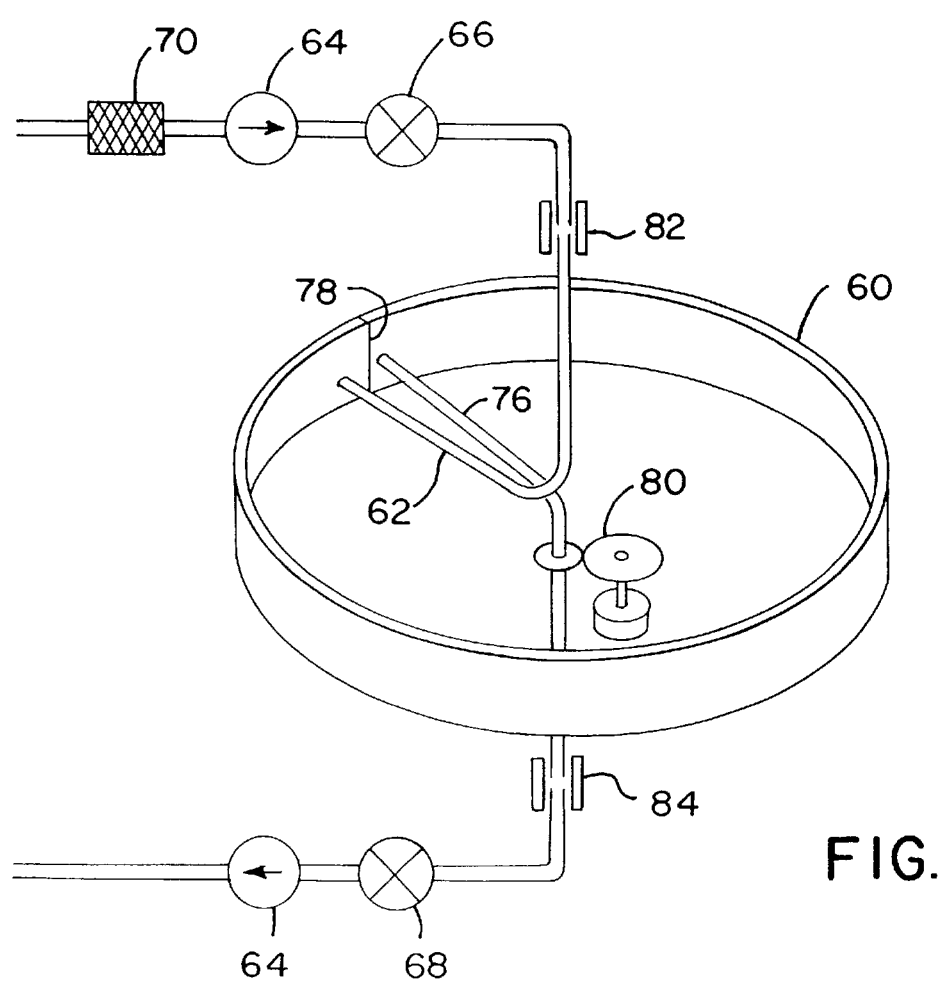
FIG. 4 is a perspective view of another embodiment of a channel assembly encompassed by the invention.
Figure 5:
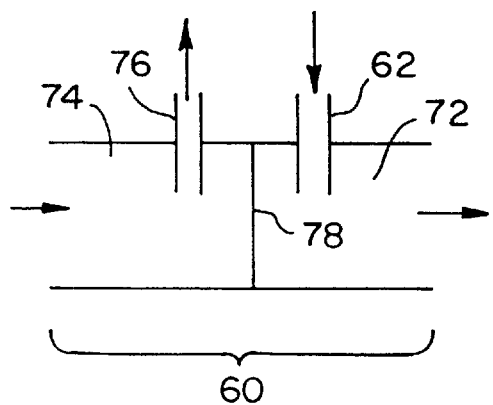
FIG. 5 is a schematic diagram of a section of the channel of FIG. 4 illustrating the channel input and outlet lines in greater detail.
Figure 6:
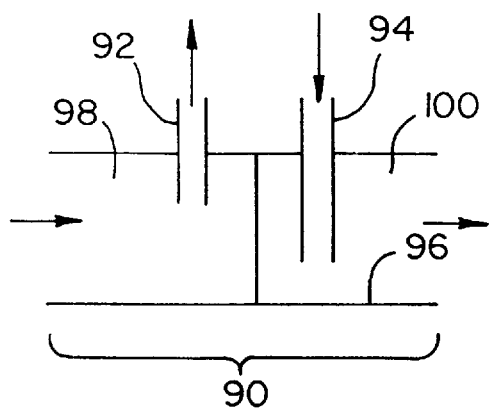
FIG. 6 is a schematic diagram of a section of an alternate embodiment of a channel illustrating the channel input and outlet lines in greater detail.

A separation channel assembly from a typical channel-type continuous flow centrifuge, used to concentrate waterborne pathogenic organisms according to the present invention, is depicted in FIG. 2 at reference numeral 30. The channel assembly 30 depicted in FIG. 2 is part of an IBM model 2997 blood separation channel centrifuge. The division of IBM which manufactured the channel assembly 30 pictured in FIG. 2 is now owned by COBE Corporation, Lakewood, Colo., USA. References of interest regarding the IBM model 2997 channel centrifuge (and/or centrifuges like it) are U.S. Pat. Nos. 4,010,894, 4,094,461, 4,387,848 and 4,430,072 to Kellogg et al.; U.S. Pat. Nos. 4,386,730, 4,439,178, 4,447,221 and 4,708,712 to Mulzet; U.S. Pat. No. 4,647,279 to Mulzet et al.; U.S. Pat. No. 4,900,298 to Langley; U.S. Pat. No. 5,496, 265 to Langley et al.; U.S. Pat. No. 4,850,995 to Tie et al.; U.S. Pat. No. 4,419,089 to Kolobow et al.; and the references cited within these patents.

When the channel assembly 30 of FIG. 2 is used as blood separator, blood from a donor's arm is continuously pumped from a radially directed input line 32, through the inner channel wall 34, and into hollow channel 36 as the channel assembly 30 rotates. The various blood components (e.g., plasma and red blood cells) are flung toward the outer channel wall 38 by centrifugal force, and they therefore separate according to their specific gravity as the blood moves around channel 36 from the input line 32 to several exit lines 40, 42, and 44 (shown in greater detail in FIG. 3). The blood cannot flow directly from the input line 32 to the output lines 40/42/44 and is forced to traverse the entirety of the channel 36 owing to the barrier 46 situated between the inlet and outlet lines 32 and 40/42/44. To collect the various layers of blood, the exit lines 40/42/44 are positioned at different radial locations spaced from the inner wall 34 of channel 36. Plasma, leukocytes (white cells), and red blood cells are each collected through respective exit lines 40, 42, and 44.

The structure and operation of continuous flow channel centrifuges may be better understood if they are compared and contrasted to the structure and operation of continuous flow bowl centrifuges. In the channel 36 of FIG. 2, blood flow is in an arcuate path centered about the rotational axis. Flow occurs entirely in planes perpendicular to the rotational axis, and the total length of the flow path subjected to centrifugal force of any appreciable magnitude is approximately 2r (in the input and exit lines 32 and 40/42/44) plus 2πr (in the channel 36), wherein r is the radial distance between the rotational axis and the inner wall 34 of the channel 36. The centrifugal force is exerted perpendicular to the channel 36, and most of the separation between heavy and light blood fractions occurs along its length, wherein the direction of blood flow is tangential to the channel 36 and in a direction perpendicular to the rotational axis.

In comparison, a continuous flow bowl-type centrifuge such as the one shown in FIG. 1 does not use a flow path curving about the rotational axis; rather, the flow path of any element of blood entering the centrifuge will be generally along a plane coincident with the rotational axis. The overall flow path has a length of 2r plus h, the 2r flow path being in the input and exit lines 24 and 26 and oriented in planes perpendicular to the rotational axis, and the h flow path being directed along the height of the bowl 22 and oriented in planes parallel to the rotational axis. Most of the separation between heavy and light blood fractions occurs along the walls of the bowl 22, wherein the direction of blood flow is generally parallel to the rotational axis.

A unique design feature of certain channel assemblies (such as the model 2997) is their rotating seal assembly 48. It consists of a stationary top half 50 and a bottom half 52 which rotates with the channel 36. The surfaces where the two halves 50 and 52 meet have four concentric matching grooves (not shown) that correspond to whole blood input line 32 and the three exit lines 40, 42, and 44. Whole blood and blood components are transferred from stationary to moving parts through the four grooves. The hydrodynamic design of the grooves and the viscosity of blood prevent the liquid from leaking between the junction of the two halves 50 and 52 of seal assembly 48, which is open to the atmosphere. Because bloodborne pathogens could potentially leak into or from the seal, blood cell separators using a rotating seal assembly have become obsolete.

Use of the Separation Channel to Concentrate Pathogenic Organisms

To concentrate pathogenic organisms such as Cryptosporidium and other protozoan parasites from potentially contaminated water in accordance with the invention, water may be fed into the channel assembly 30 illustrated in FIGS. 2 and 3, which is operated as a simple continuous-flow centrifuge. However, prior to sending water through the channel, several preliminary steps are preferred.

First, the channel 36 and associated tubing are preferably primed with water containing a surfactant, for example 0.001% Tween 80 or Tween 20 (Sigma Chemical Co., St. Louis, Mo., USA), to enhance removal of the collected material containing the organisms after centrifugation is completed. Priming may be conducted with an output pump (not shown), the plasma pump built into the centrifuge, or a separate additional peristaltic pump (as discussed below). Priming with a surfactant is not performed if the channel assembly 30 is used for blood separation.

Second, when a centrifuge using the channel assembly 30 is used as a blood separator, donor safety sensors (not shown) within the centrifuge test the tubing of the channel assembly 30 for air emboli and pressure irregularities. When the channel assembly 30 is instead used to concentrate pathogenic organisms, the sensors and unnecessary pumps and circuits may be disabled or removed.

Third, when channel assemblies 30 having the split-seal arrangement 48 are used, water containing 50% glycerin (or another viscosity-modifying substance) is pumped into the saline line (not shown) of rotating seal assembly 48 using a lubricant pump (not shown) operating at a speed of about 2.5 rpm. The glycerin creates a viscous barrier between water and air at the junction of the two halves 50 and 52 of seal assembly 48 to prevent leaking. Glycerin is not used when split-seal channel centrifuge assemblies are used as blood separators because blood is normally sufficiently viscous to move between stationary and moving halves 50 and 52 without leaking. If channel assemblies with newer valves (i.e., non-split-seal valves) are used, the viscosity modification is unnecessary.

Water potentially contaminated by dilute densities of pathogenic organisms is then fed into channel 36 via whole blood input line 32 at a flow rate in the range of between about 70 mL/min to 500 mL/min, and preferably about 150 mL/min. The water is centrifuged at a speed such that the relative gravitational force inside the channel 36 is about 900 xg, which equates to approximately 2400 rpm for the IBM model 2997 channel assembly 30. Centrifugation is performed for a period of time sufficient to process a predetermined sample volume.

After centrifugation, the organisms, inorganic sediment, and detritus are retained in channel 36 rather than being pumped out, as is customary with red blood cells when blood separation is performed. The supernatant (water) is pumped out via plasma exit line 40.

Experimental Results

Initial experiments to test the feasibility of channel assembly 30 for concentrating and collecting pathogenic organisms from water will now be summarized. An aqueous medium was spiked with a microorganism, usually Cryptosporidium, at a known concentration. The medium was then centrifuged by use of a continuous flow channel centrifuge. Except for experiments 6, 7 and 8 summarized below, the aforementioned model 2997 channel assembly 30 was used.

Several tests were conducted at the maximum sample feed rate of the built-in plasma pump, about 70 mL/min. Other tests used a separate peristaltic pump which was not part of channel assembly 30 and which was capable of providing a maximum sample flow rate of 500 mL/min. Centrifugation took a few minutes to several hours depending on the water sample volume. The processing time is normally calculated as the sample volume divided by the sample feed rate, and in general, the centrifugation time necessary to concentrate protozoa from typical water samples will be on the order of about ½ to 4 hours when the model 2997 channel assembly 30 is used. For smaller samples, lesser times are sufficient.

After centrifugation was complete, the input and exit lines 32 and 40/42/44 from seal assembly 48 to channel 36 were carefully clamped, the channel 36 removed from the rotor, and the contents drained into a beaker. The channel 36 was carefully cut in half so that its contents were not spilled, and its cut ends were then clamped with VISE GRIP pliers. Each half of the channel 36 was then filled with 0.01% Tween 80 and its ends were clamped shut. The channel 36 was then shaken vigorously and placed on a laboratory vortex to dislodge any Cryptosporidium that may have adhered to the channel. This rinsing procedure was conducted several times. The concentrate and all rinses were combined. For these feasibility studies, no further steps were taken to separate Cryptosporidium from debris in the water. The combined concentrate and rinses were then examined for Cryptosporidium oocysts and/or other cysts by use of the Merifluor Detection Kit, an immunofluorescent assay produced by Meridian Diagnostics, Cincinnati, Ohio. All results are reported as percent recovery, i.e. total number of organisms recovered in the channel divided by the number added to the medium, multiplied by 100.

EXPERIMENT 1

Recovery of Cryptosporidium Oocysts from Phosphate-Buffered Saline Solution

Phosphate-buffered saline (PBS) is a simpler aqueous medium than naturally occurring surface or ground water, and therefore would presumably present optimum conditions for concentrating Cryptosporidium oocysts by a continuous flow channel centrifuge. Apart from testing oocyst recovery at these theoretically optimum conditions, the experiment tested whether recovery efficiency varied with oocyst concentration, an important consideration given the range of oocyst densities that exist in the environment.

Cryptosporidium oocysts from the positive control of the Merifluour Detection Kit were diluted with 10% formalin to make a working stock solution having a concentration of approximately 5000 oocysts/mL. Oocysts were spiked into 2 or 5 L of PBS to achieve the following four target concentrations: 1000, 100, 20 or 5 oocysts/L. The IBM 2997 blood cell separator was used as the continuous flow channel centrifuge. The centrifuge feed rate was set at 70 ml/min, and the rotor speed was 2200 rpm (relative centrifugal force of 740 xg). The total centrifuge time was ½ to 1 hour per sample. The recovery efficiency of the centrifuge was tested 3 to 5 times at each oocyst concentration.

The material from the channel was tested for oocyst presence. The supernatant remaining in the channel after centrifugation was also collected, concentrated by bulk centrifugation at 10000 xg for 15 min, and the pellets were analyzed for oocysts in the same manner. The results show that Cryptosporidium recoveries of greater than 69% were achieved, and that, most importantly, a recovery of nearly 100% was achieved for the most dilute oocyst concentration (5 oocysts/L):

| Oocysts/Liter | No. of Tests | Mean % Recovery | Std. Dev. % Recovery |
|---|---|---|---|
| 100 | 3 | 84.4 | 15.7 |
| 1000 | 4 | 68.5 | 5.7 |
| 20 | 5 | 93.8 | 33.0 |
| 5 | 3 | 98.8 | 16.7 |

EXPERIMENT 2

Recovery of Cryptosporidium Oocysts from Pond Water

To more closely simulate the conditions under which the invention would operate when concentrating naturally occurring Cryptosporidium, live oocysts were spiked into pond water. Recovery efficiencies were compared with those attained using PBS and between two oocyst concentrations in pond water.

Purified live Cryptosporidium oocysts were obtained from Parasitology Research Labs (Phoenix, Ariz., USA) and diluted with distilled water for a working stock concentration of approximately 15,000 oocysts/mL. Oocysts were spiked by adding the appropriate volume of stock solution to 100 mL of pond water, fixing the Cryptosporidium with formalin (10% final concentration), then mixing the 100 mL aliquot in the larger pond water volume to be centrifuged. These steps were taken to insure that the organisms were killed while minimizing the amount of added formalin.

Cryptosporidium oocysts were spiked into 2, 10, or 15 liters of pond water, collected from the same local pond (Pond 1) on the day of centrifugation. Water was collected from the pond surface with 5 gallon buckets where the water depth was at least 50 cm. Collection of bottom sediments was avoided. The sampled pond water had 49 mg/L total solids and turbidity of 2.1 NTU.

Ten liters of water from Pond 1, without added oocysts, were centrifuged as a control. Indigenous Cryptosporidium oocysts were not found. Oocyst target concentrations were 1000 or 100 oocysts/L. The centrifuge feed rate was set at 70 mL/min, and the rotor speed was 2400 rpm (generating approximately 900 xg of force). Centrifuge times were ½ to 3 ½ hours. The recovery efficiency was tested 3 times at each oocyst concentration.

The results, presented below, show recoveries of 100% for the most dilute oocyst concentration (100 oocysts/L). The percentage recoveries were calculated based on the concentration of oocysts retained in the channel as compared to the amount of the initial spiking. The supernatants were also examined for oocysts not retained by the centrifuge. Except for the sample feed rates of 250 and 500 ml/min described in Example 3 below, no oocysts were detected in any of the supernatants. Thus, it is most likely that organism separation in the channel was close to 100%, and the apparent loss of organisms from the concentrate to be tested probably arises due to other steps in the process (e.g., during use of the immunofluorescent assay).

| Oocysts/Liter | No. of Tests | Mean % Recovery | Std. Dev. % Recovery |
|---|---|---|---|
| 100 | 3 | 102.9 | 5.6 |
| 1000 | 3 | 90.3 | 10.8 |

EXPERIMENT 3

Recovery of Cryptosporidium Oocysts as a Function of Sample Feed Rate

The time required to concentrate oocysts by continuous flow centrifugation depends on the sample volume and the sample feed rate into the centrifuge. Given the maximum relative centrifugal force generated by the blood cell separator (900 xg), this experiment was conducted to determine the maximum sample feed rate that could be used without reducing recovery efficiency.

Purified live Cryptosporidium oocysts were used as described in Experiment 2. Cryptosporidium oocysts were spiked into 2 or 10 L of water from Pond 1. The target concentration of oocysts was 1000/L for all centrifugation runs. Percent recovery was measured at three sample feed rates: 150, 250, and 500 ml/min. Centrifugation times were 4 minutes to 1 hour.

Samples were pulled into the channel at the desired rate by a peristaltic pump (Cole Parmer model 7553-20) placed downstream from the channel. The built-in centrifuge pumps were bypassed because their maximum pumping rate is only 70 ml/min. Recovery efficiencies were measured 3, 4 or 5 times at each sample feed rate.

The results, presented below, show recovery rates of between 45–95%, with the highest recovery achieved at the lowest flow rate tested (150 mL/min).

| Pump Speed mL/min | No. of Tests | Mean % Recovery | Std. Dev. % Recovery |
|---|---|---|---|
| 150 | 3 | 94.4 | 5.9 |
| 250 | 3 | 70.3 | 6.0 |
| 500 | 5 | 43.3 | 5.5 |

EXPERIMENT 4

Recovery of Cryptosporidium From Pond Water, Sample Feed Rate=150 mL/min

Having observed in Experiment 3 that oocysts could be recovered efficiently when the sample feed rate is 150 mL/min, this example tested whether the recovery efficiency changed with oocyst concentration at that feed rate.

Purified live Cryptosporidium oocysts were used as described in Experiment 2. Cryptosporidium oocysts were spiked into 10 or 25 L of water from another local pond, here denoted Pond 2. For Pond 2, total solids were 182 mg/L, and turbidity was 8.3 NTU.

Ten liters of water from Pond 2 without added oocysts was centrifuged as a control. Indigenous Cryptosporidium oocysts were not found.

Target concentrations were 1000, 100 or 20 oocysts/L. The independent peristaltic pump pulled the samples into the IBM 2997 centrifuge at a flow rate of 150 mL/min. The rotor speed was 2400 rpm (900 g). The time for centrifugation was one to three hours. Recovery efficiencies were measured 3 or 4 times at each Cryptosporidium concentration.

Supernatants were tested as described in Experiment 1. The results, presented below, show Cryptosporidium recoveries of between 80% and nearly 100%, with the highest recovery achieved at an oocyst concentration of 100 oocysts/L.

| Oocysts/Liter | No. of Tests | Mean % Recovery | Std. Dev. % Recovery |
|---|---|---|---|
| 100 | 4 | 100.8 | 15.1 |
| 1000 | 3 | 97.2 | 9.6 |
| 20 | 3 | 77.9 | 17.9 |

EXPERIMENT 5

Recovery of Giardia Cysts From Pond Water

The centrifugation process was tested with *Giardia lamblia*, another waterborne protozoan pathogen, to assess whether the centrifuge could efficiently concentrate pathogens larger than Cryptosporidium.

Purified live Giardia cysts were obtained from Parasitology Research Labs (Phoenix, Ariz., USA) and diluted with distilled water to approximately 22,000 cysts/mL. Cysts were added to water from Pond 2 following the same procedure for Cryptosporidium described in Experiment 2.

Ten liters of water from Pond 2, without added cysts, were centrifuged as a control. Indigenous Giardia cysts were not found. Giardia cysts were spiked into 10 or 30 L of pond water. Target concentrations of Giardia cysts were 1000, 100 or 20/L. The centrifuge setup was the same as described in Experiment 4. Sample feed rate was 150 mL/min, and the rotor speed was 2400 rpm. Centrifuge time was 1 to 3 ½ hours. Recovery efficiencies were measured 3 times at each Giardia concentration.

The results, presented below, show recoveries of Giardia cysts to be between 90–100%.

| Target Concentration Oocysts/Liter | No. of Tests | Mean % Recovery | Std. Dev. % Recovery |
|---|---|---|---|
| 100 | 3 | 94.6 | 5.2 |
| 1000 | 3 | 104.2 | 5.7 |
| 20 | 3 | 97.0 | 10.5 |

EXPERIMENT 6

COBE Spectra Centrifuge

The COBE Spectra centrifuge is a newer continuous flow channel centrifuge for use in blood cell separation. Unlike the IBM 2997 centrifuge discussed above, there is no rotating ceramic seal. The channel itself has a hoop-shaped geometry similar to the channel 36 of FIG. 2.

Purified live Cryptosporidium oocysts were used as described in Experiment 2. Oocysts were spiked into 5 or 7.5 L of water from Pond 2. The oocyst target concentration was 100/L for all centrifuge runs. The input pump of the COBE Spectra centrifuge was set at 150 mL/min, and the rotor speed was 2400 rpm (900 xg). The recovery efficiency was tested 3 times.

Using the COBE centrifuge to concentrate Cryptosporidium, 100% of the spiked Cryptosporidium oocysts were recovered.

Figure 7:
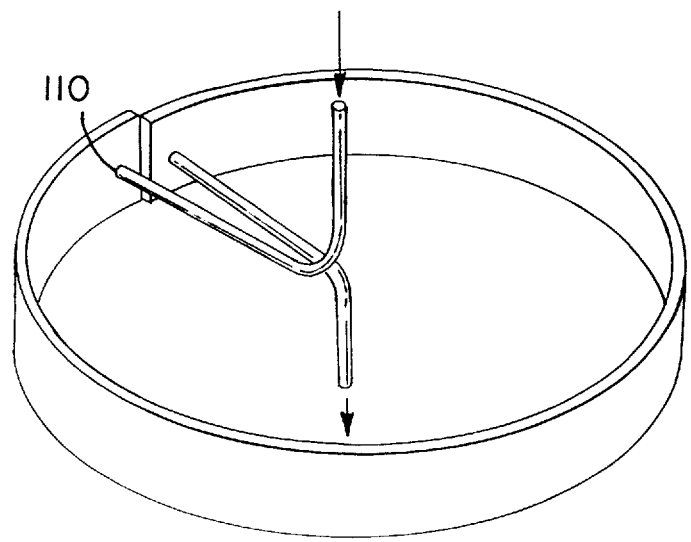
FIGS. 7–11 are perspective views of alternate embodiments of channel assemblies encompassed by the invention.

| Oocysts/Liter | No. of Tests | Mean % Recovery | Std. Dev. % Recovery |
|---|---|---|---|
| 100 | 3 | 103.3 | 14.8 |

EXPERIMENT 7

Recovery of Cryptosporidium Oocysts as a Function of Water Turbidity

An effective method for concentrating pathogenic organisms from water must work over a wide range in water turbidity. In this experiment turbidity was manipulated by concentrating seston in pond water by bulk centrifugation (10,000 xg for 15 minutes). For example, to increase turbidity 10-fold above ambient, 10 volumes of pond water were concentrated and the seston pellets added and mixed to the unit volume to be spiked with oocysts. Turbidity was measured using a fluorescence spectrophotometer (Hitachi Model F-4500, excitation and emission wavelengths=500.0 nm, slit width=2.5 nm, and PMT voltage=400 V). Oocysts were spiked into 7.5 L pond water, as described in Experiment 2, at a target concentration of 100 oocysts/L. Oocysts were recovered with the COBE Spectra centrifuge (rotor speed =2400 rpm or approximately 900 xg, sample feed rate=150 mL/min).

The results, presented below, show that percent recovery of oocysts did not vary with turbidity levels between 2.6 and 30.8 NTU (F statistic, $p>0.05$, comparison based on count aliquots ($n=6$) because turbidity levels could not be replicated).

| Turbidity (NTU) | No. of Tests | Mean % Recovery | Std. Dev. % Recovery |
|---|---|---|---|
| 2.6 | 6 | 84.9 | 17.0 |
| 4.8 | 6 | 81.5 | 27.7 |
| 8.6 | 6 | 92.2 | 20.1 |
| 15.7 | 6 | 93.8 | 29.9 |
| 20.1 | 6 | 101.2 | 40.9 |
| 30.8 | 6 | 82.3 | 29.3 |

EXPERIMENT 8

Recovery of Cryptosporidium from Large Pond Water Volumes

Given that waterborne pathogenic organisms may occur in dilute densities, an effective concentration method must be able to process a large sample volume, on the order of 100 liters. In this experiment live and purified Cryptosporidium oocysts were spiked into 100 L of pond water. Spiking was conducted as described for Experiment 2. The target density was 100 oocysts/L. Oocysts were recovered with the COBE Spectra centrifuge (rotor speed=2400 rpm or approximately 900 g, sample feed rate=150 mL/min). Centrifugation time for this rotor speed and sample feed rate was 11 hours.

Mean percent recovery of Cryptosporidium oocysts from 100 L of pond water was 94.7±9.7% (mean±1 standard deviation, $n=3$). The recovery efficiency was not significantly different than recovery with the centrifuge and a sample volume of 5 to 7 L (two-tailed t test, $p>0.05$), as performed in Experiment 6.

Modifications and Alternate Embodiments

Another embodiment of a channel suitable for use in concentrating dilute densities of pathogenic organisms from water is illustrated in FIGS. 4 and 5. The channel 60 includes an input line 62 downstream of a pumping means 64 for supplying potentially contaminated water to the channel 60. This pumping means 64 is a source of static or dynamic pressure head, i.e., a pump, tank, or other water sources which generate water flow into the input line 62. Pressure restriction/flow control valves can be provided upstream and/or downstream of the channel 60, as illustrated at 66 and 68. A coarse sediment filter 70 may also be placed upstream from the channel 60, to remove any gross impurities from the input line 62 before they enter the channel 60 and clog it. Water flows from the input line 62, into the channel entry 72, and then through the channel 60 (not fully shown in FIG. 5) to the channel end 74. The water then exits the channel 60 from the exit line 76, which may have a downstream pumping means in addition to (or in place of) the pumping means 64 upstream of the input line 62. As shown in FIG. 5, the channel end 74 and channel entry 72 are separated by a barrier 78 so that water can only reach the exit line 76 from the input line 62 after flowing through the entirety of the channel 60. The centrifuge drive is depicted at 80. The principal difference between the apparatus of FIGS. 4 and 5 from that of FIGS. 2 and 3 is that the channel 60 need only include a single exit line 76 rather than several, since separation of the input water into multiple fractions of different density will generally not be of interest. Additionally, the split-seal valving arrangement (and thus the necessity for adding a viscosity modifier) is avoided by having the input and exit lines 62 and 76 extend axially to join high-speed rotary seals 82 and 84.

Another embodiment of a channel suitable for use in concentrating dilute densities of pathogenic organisms from water is illustrated in FIG. 6. The channel 90 of FIG. 6 differs from that of FIGS. 2-3 in several important respects. First, it need only include a single exit line 92 rather than several. Second, the input line 94 is located radially outward of the exit line 92, rather than at a radially inward or radially equivalent position. The use of a radially inwardly located exit line 92 helps to prevent organisms from being carried directly to the input line 94 to the exit line 92 by the water flow, or from being diverted to the exit line 92 due to turbulence in the channel, because the organisms will be more likely to settle radially outwardly to the outer channel wall 96 by the time they reach the channel end 98. In other words, immediately upon entering the channel entry 100 via the input line 94, the heavier organisms will begin traveling toward the outer channel wall 96 and are less likely to defeat the force gradient to exit the exit line 92. The input line 94 can be radially positioned inward of the exit line 92 by simply fixing the input and exit lines 94 and 92 in this location, as shown in FIG. 6. Alternatively (or additionally), this be done by modifying the shape of the channel so that the channel end 98 is located radially inward of the channel entry 100, as by modifying the channel into a generally spiral shape rather than an annular shape. In this configuration, which is shown in FIG. 7, the highest centrifugal force vectors are exerted on the organisms near the channel entry 110.

Figure 8:
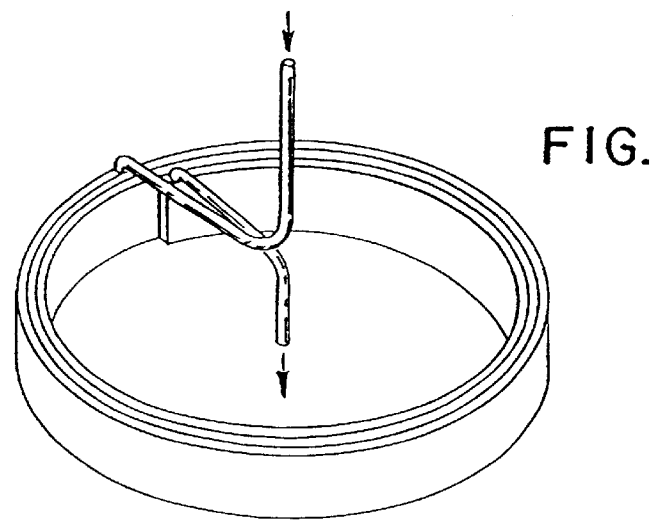
Figure 9:
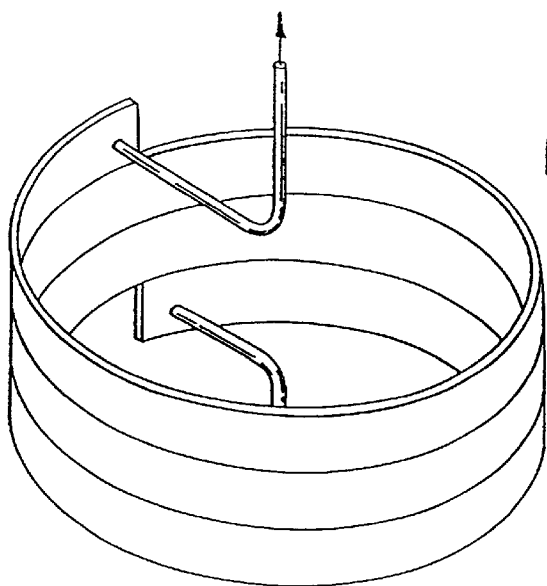

Regarding the modification of the channel into a spiral shape, it is noted that embodiments such as that of FIG. 8 are possible wherein a horizontal spiraling configuration allows for a channel of much greater length, and thus much greater residence time for the water flowing therein. The vertical spiraling configuration of FIG. 9 is another possibility. The longer channels provided by these embodiments may help in further concentration of organisms.

Figure 10:
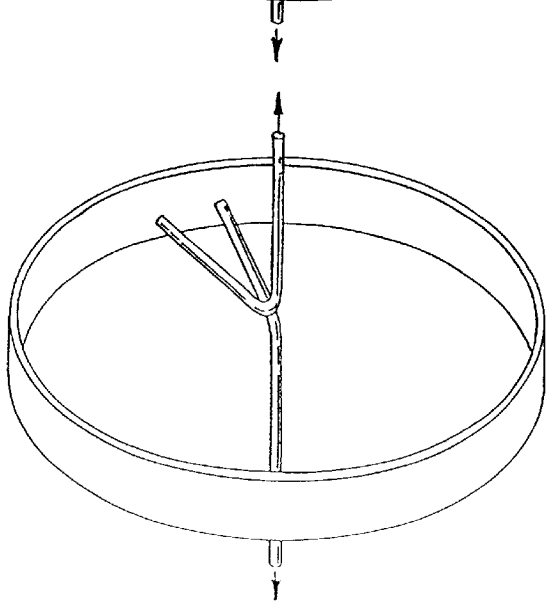

It is also possible to modify the shape of the channel into a generally elliptical configuration, as shown in FIG. 10. Configurations of this type may be helpful in that higher concentrations of organisms may gather at the areas wherein the channel intersects the major axes of the ellipse, since these are the areas where the maximum centrifugal forces are exerted on the water.

Figure 11:
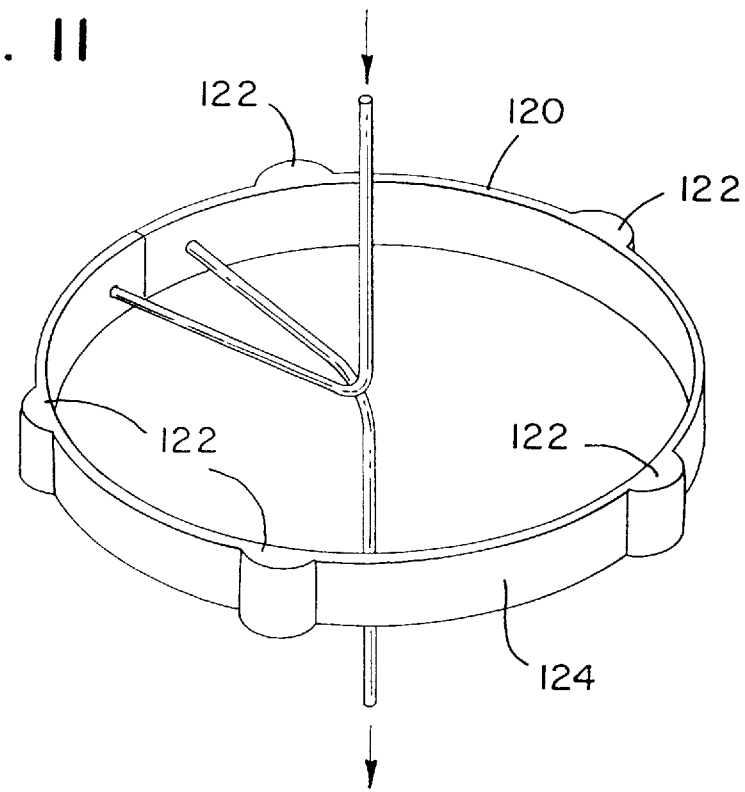
Figure 12:
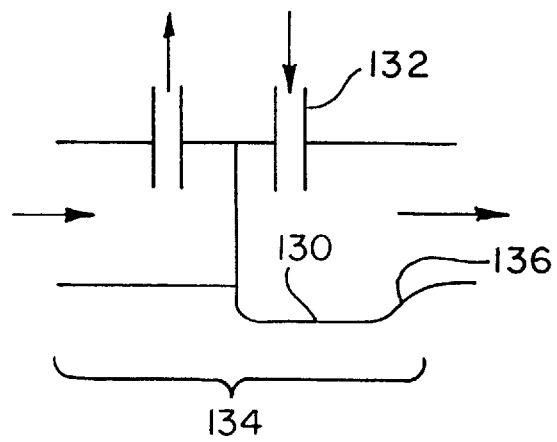
FIG. 12 is a schematic diagram of a section of an alternate embodiment of a channel illustrating the channel input and outlet lines in greater detail.

In similar fashion, it may be helpful to form a series of depressions in the outer wall of the channel, as exemplified in the channel 120 of FIG. 11. These depressions form traps 122 which may catch and retain organisms to a greater degree than the surrounding regions on the outer channel wall 124, which are located more radially inward.

Strategic placement of these traps may lead to other beneficial results as well. As an example, FIG. 12 provides a closer view of a trap 130 opposite the input line 132. A trap 130 at or near this location is recommended when more turbid water is being tested, not so much for the purpose of capturing organisms, but for capture of sand and other very heavy detritus. Upon entering the channel 134, these heavy gross impurities will rapidly fall into the trap 130, thus providing for "cleaner" collection of organisms in downstream channel areas. However, if any traps 130 or other discontinuities are formed in any of the walls of the channel 134, care must be taken to form them in such a manner that they do not generate undue turbulence in the water flow (hence the gently sloping downstream surface 136 of the trap 130 shown in FIG. 12). Such turbulence may dislodge organisms from the channel walls or redivert a settling organism into a flow path located further radially inward, and this could result in organisms escaping the channel 134.

It may also be helpful to form the aforementioned traps 130/136 with transparent walls so that the contents of the traps 130/136 will be visible to centrifuge operators when the channel is at rest. Such traps would also be visible when the channel is spinning if used in conjunction with a strobe.

It is noted that while the invention has generally been described with reference to a channel having a duct-like fully enclosed flow passageway, the channels described in this disclosure are not confined to this form. Consider, for example, that the inner channel wall 34 of the channel 36 of FIGS. 2 and 3 is not absolutely necessary if fluid addition, fluid withdrawal, and channel flushing all occur while the channel 36 is rotating at high speed: since the liquid is flung radially outward against the outer channel wall 38 by centrifugal force, the inner channel wall 34 would not restrain the liquid or have any other practical effect on the liquid. Similarly, the overall shape of the channel—whether circular, elliptical, or spiral, and whether oriented entirely within the same plane or in multiple planes (as in the vertical spiral configuration illustrated in FIG. 9)—is not critical, though it can provide desirable results if properly chosen. What is regarded to be important is the introduction of potentially-contaminated water into a continuous flow centrifuge wherein the flow is generally tangentially oriented over at least a section of the flow path. (In this disclosure, when a section of a flow path is stated to have "tangential" or "tangentially oriented" flow, this is intended to mean that when this section of the flow path is viewed from a direction coincident with the rotational axis, the instantaneous direction of liquid flow at each location along the section is at least substantially coincident with or parallel to the instantaneous direction of motion of the liquid at that location owing to rotation. As an example, the hoop-like channel of FIG. 2 has tangential flow.) In a continuous flow centrifuge utilizing generally tangential flow, this is best met by situating the input and exit lines substantially near the ends of the flow path. Thus, the optimal hoop-shaped channel for use in concentrating pathogenic organisms would use closely-spaced input and exit lines connected to the channel, with the channel having a barrier between the input and exit lines to force the water to flow through the full extent of the channel. Such a barrier need not fully close the channel; rather, it need only extend radially inward from the outer channel wall to such an extent that the water, when input at a given flow rate and when subjected to centrifugal forces, resides at a height lower than the height of the barrier (this "height" being measured in the radial direction).

However, there is a factor that is regarded to be of potential importance regarding the form of the channel. It is believed that forming the channel to better maintain laminar flow conditions therein, as by removing any sharp convergences, divergences, or discontinuities within the channel, will result in better recovery of organisms. Turbulence may allow the organisms to defeat centrifugal force gradients within the channel and allow the organisms to escape the channel's exit line. Laminar flow may also be encouraged by maintaining a lower flow rate through the channel, though higher flow rates are of course preferred for obtaining lesser testing times with larger sample throughput.

As noted above, it is believed that longer channels (flow paths) are believed to yield better organism recovery. However, it is conceivable to have a channel with a shorter flow path than the channels described above, as in the case of a channel which occupies only a subsection (arc) of a path curving about the rotational axis, or a circular channel wherein the inlet and exit lines are spaced apart with no barrier situated between so that two shorter flow paths are effectively formed, each having an opposite flow direction. While these would likely result in at least partial recovery of organisms, it is believed that they would not attain the same degree of recovery as a standard hoop-like channel operating under similar conditions. It is suggested in any case that channels used in accordance with the invention have flow paths with lengths greater than 2r, where r is the radial distance from the rotational axis to the inner wall of the channel, and preferably a length approaching $2\pi r$. In the case of spiral, elliptical, or other noncircular channels, this relationship is interpreted to have r be the average of the maximum and minimum radial distances from the rotational axis to the inner wall of the channel.

At some point, it may be desirable to concentrate pathogenic organisms which are lighter than water, as where the organisms have accumulated large amounts of intracellular lipids. In this case, the teachings set out above may still be applied with thought being given to the result to be achieved; for example, the input/exit line arrangement of FIG. 6 may be modified to have the input line located radially inward of the exit line, the traps of FIGS. 11 and 12 may be located on the inner channel wall rather than the outer channel wall, and so on.

The invention can be installed in preexisting water treatment facilities to provide sampling of water for pathogenic organisms. For example, the invention can be used in series or parallel with the water intake of a treatment facility to provide continuous sampling for pathogenic organisms, thereby replacing the current time-consuming method of periodically spot-checking the water. In this arrangement, it may be useful to install a known flow restrictor/pressure limiting valve upstream or downstream of the centrifuge to maintain the flow rate at a desired cutoff value, and/or install an upstream coarse sediment filter to avoid potential clogging by gross impurities (as illustrated in FIG. 4).

One of ordinary skill in the art will comprehend that while this disclosure has mainly described the application of the invention to concentration of Cryptosporidium (and to a lesser extent Giardia), the invention is expected to be equally applicable to other concentration of other protozoa, as well as other waterborne pathogenic organisms in general, since generally the same considerations will apply.

It is understood that preferred embodiments of the invention have been described above in order to illustrate how to make and use the invention. The invention is not intended to be limited to these embodiments, but rather is intended to be limited only by the claims set out below. Thus, the invention encompasses all alternate embodiments that fall literally or equivalently within the scope of these claims. It is understood that in the claims, means plus function clauses are intended to encompass the structures described above as performing their recited function, and also both structural equivalents and equivalent structures. As an example, though a nail and a screw may not be structural equivalents insofar as a nail employs a cylindrical surface to secure parts together whereas a screw employs a helical surface, in the context of fastening parts, a nail and a screw are equivalent structures.

What is claimed is:

1. A method of concentrating pathogenic organisms from water comprising the steps of:

a. continuously feeding the water into an elongated flow path, the flow path including a separation section wherein the water flows in an arcuate path about a rotational axis in directions which are substantially tangential with respect to the rotational axis, the separation section having a length greater than 2r, where r is the average of the maximum and minimum radial distances of the flow path from the rotational axis; and b. subjecting the flow path to centrifugal forces by spinning the flow path about the rotational axis, wherein the centrifugal forces are substantially perpendicular to the separation section.

2. The method of claim 1 wherein after spinning the flow path, the water therein is tested for the presence of pathogenic organisms.

3. The method of claim 1 wherein the water flow is laminar throughout substantially all of the separation section.

4. The method of claim 1 wherein the flow path is coated with a surfactant.

5. The method of claim 1 wherein the centrifugal forces create a relative gravitational force within the separation section of at least 900 xg.

6. The method of claim 1 wherein the flow path includes a water input line and a water exit line, each situated near an end of the flow path.

7. The method of claim 6 wherein the input and exit lines are adjacent each other on the flow path with a barrier resting therebetween.

8. The method of claim 6 wherein at least one of the input and exit lines is substantially radially oriented toward the rotational axis.

9. The method of claim 1 wherein the separation section includes a point on the flow path which is spaced at the maximum radial distance from the rotational axis.

10. The method of claim 1 wherein the separation section has a length greater than 2πr.

11. The method of claim 1 wherein the flow path is defined by a channel centrifuge.

12. The method of claim 1 wherein the pathogenic organisms are protozoa.

13. A method of concentrating pathogenic organisms from water comprising the steps of:

a. continuously feeding the water into an elongated flow path, the flow path including a separation section wherein the water flow is oriented in directions substantially tangential with respect to a rotational axis; and b. subjecting the flow path to centrifugal forces by spinning the flow path about the rotational axis, wherein the centrifugal force is substantially perpendicular to the separation section.

14. The method of claim 13 wherein after spinning, the water in the flow path is tested for the presence of pathogenic organisms.

15. The method of claim 13 wherein the water flow is laminar throughout substantially all of the separation section.

16. The method of claim 13 wherein the flow path is coated with a surfactant.

17. The method of claim 13 wherein the centrifugal force creates a relative gravitational force within the separation section of at least 900 xg.

18. The method of claim 13 wherein the separation section follows an arcuate path defined about the rotational axis.

19. The method of claim 13 wherein the flow path includes a water input line and a water exit line, each situated near an end of the flow path.

20. The method of claim 19 wherein the input and exit lines are adjacent each other on the flow path with a barrier resting therebetween.

21. The method of claim 19 wherein at least one of the input and exit lines is substantially radially oriented toward the rotational axis.

22. The method of claim 13 wherein the separation section includes a point on the flow path which is spaced at the maximum radial distance from the rotational axis.

23. The method of claim 13 wherein the separation section has a length greater than 2r, where r is the average of the maximum and minimum radial distances of the flow path from the rotational axis.

24. The method of claim 23 wherein the separation section has a length greater than 2πr.

25. The method of claim 13 wherein the flow path is defined by a channel centrifuge.

26. The method of claim 13 wherein the pathogenic organisms are protozoa.

27. A method of concentrating pathogenic organisms from water comprising the steps of:

a. continuously feeding the water into an elongated flow path, the flow path including a separation section wherein the water flows in an arcuate path about a rotational axis; and b. subjecting the flow path to centrifugal forces by spinning the flow path about the rotational axis, wherein the centrifugal force is substantially perpendicular to the separation section.

28. The method of claim 27 wherein after spinning the flow path, the water therein is tested for the presence of pathogenic organisms.

29. The method of claim 27 wherein the water flow is laminar throughout substantially all of the separation section.

30. The method of claim 27 wherein the flow path is coated with a surfactant.

31. The method of claim 27 wherein the centrifugal force creates a relative gravitational force within the separation section of at least 900 xg.

32. The method of claim 27 wherein the flow path includes a water input line and a water exit line, each situated near an end of the flow path.

33. The method of claim 32 wherein the water input and exit lines are adjacent each other on the flow path with a barrier resting therebetween.

34. The method of claim 32 wherein at least one of the input and exit lines is substantially radially oriented toward the rotational axis.

35. The method of claim 27 wherein the separation section includes a point on the flow path which is spaced at the maximum radial distance from the rotational axis.

36. The method of claim 27 wherein the separation section has a length greater than 2r, where r is the average of the maximum and minimum radial distances of the flow path from the rotational axis.

37. The method of claim 36 wherein the separation section has a length greater than $2\pi r$.

38. The method of claim 27 wherein the flow path is defied by a channel centrifuge.

39. The method of claim 27 wherein the pathogenic organisms are protozoa.

40. A method of concentrating pathogenic organisms from water comprising the steps of:

a. continuously feeding the water into a flow path, the flow path including a separation section oriented within planes generally perpendicular to the axis of rotation, and wherein the separation section has a length greater than 2r, where r is the average of the maximum and minimum radial distances of the flow path from the rotational axis; and b. subjecting the flow path to centrifugal forces by spinning the flow path about the rotational axis.

41. The method of claim 40 wherein the separation section has a length greater than $2\pi r$.

42. The method of claim 40 wherein after spinning the flow path, the water therein is tested for the presence of pathogenic organisms.

43. The method of claim 40 wherein the water flow is laminar throughout substantially all of the separation section.

44. The method of claim 40 wherein the flow path is coated with a surfactant.

45. The method of claim 40 wherein the centrifugal force creates a relative gravitational force within the separation section of at least 900 xg.

46. The method of claim 40 wherein the flow path includes a water input line and a water exit line, each situated near an end of the flow path.

47. The method of claim 46 wherein the input and exit lines are adjacent each other on the flow path with a barrier resting therebetween.

48. The method of claim 46 wherein at least one of the input and exit lines is substantially radially oriented toward the rotational axis.

49. The method of claim 40 wherein the separation section includes a point on the flow path which is spaced at the maximum radial distance from the rotational axis.

50. The method of claim 40 wherein the flow path is defined by a channel centrifuge.

51. The method of claim 40 wherein the pathogenic organisms are protozoa.

* * * * *

UNITED STATES PATENT AND TRADEMARK OFFICE
CERTIFICATE OF CORRECTION

PATENT NO : 5,858,251
DATED : January 12, 1999
INVENTOR(S): Mark A. Borchardt and Susan K. Spencer It is certified that error appears in the above-identified patent and that said Letters Patent is hereby corrected as shown below:

In claim 38, column 17, line 33, please delete "defied" and insert therefor --defined--.

Signed and Sealed this

Twentieth Day of July, 1999

*Attest:*

Q. TODD DICKINSON

*Attesting Officer*     *Acting Commissioner of Patents and Trademarks*